(12) United States Patent
Seiki et al.

(10) Patent No.: US 9,149,769 B2
(45) Date of Patent: Oct. 6, 2015

(54) DEHYDRATION SYSTEM AND DEHYDRATION METHOD

(75) Inventors: Yoshio Seiki, Hiroshima (JP); Atsuhiro Yukumoto, Hiroshima (JP); Hiroyuki Osora, Hiroshima (JP); Haruaki Hirayama, Mihara (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 550 days.

(21) Appl. No.: 12/522,831

(22) PCT Filed: Mar. 14, 2008

(86) PCT No.: PCT/JP2008/054790
§ 371 (c)(1),
(2), (4) Date: Jul. 10, 2009

(87) PCT Pub. No.: WO2008/111672
PCT Pub. Date: Sep. 18, 2008

(65) Prior Publication Data
US 2010/0219128 A1 Sep. 2, 2010

(30) Foreign Application Priority Data
Mar. 15, 2007 (JP) .................... 2007-066287

(51) Int. Cl.
*B01D 61/12* (2006.01)
*B01D 61/04* (2006.01)
(Continued)

(52) U.S. Cl.
CPC .............. *B01D 61/362* (2013.01); *B01D 63/06* (2013.01); *C07C 29/76* (2013.01);
(Continued)

(58) Field of Classification Search
None
See application file for complete search history.

(56) References Cited

U.S. PATENT DOCUMENTS

| 3,608,610 A | 9/1971 | Greatorex et al. |
| 4,895,989 A | 1/1990 | Sander et al. |

(Continued)

FOREIGN PATENT DOCUMENTS

| GB | 2170219 A | 7/1986 |
| JP | 44-9443 B | 5/1969 |

(Continued)

OTHER PUBLICATIONS

Japanese Office Action dated Jul. 28, 2008 (mailing date), issued in corresponding Japanese Patent Application No. 2007-066287.

(Continued)

*Primary Examiner* — Dirk Bass
(74) *Attorney, Agent, or Firm* — Westerman, Hattori, Daniels & Adrian, LLP

(57) ABSTRACT

A dehydration system has improved membrane performance. The dehydration system includes a dehydrating apparatus 1 comprising, in a dehydrating apparatus body, a water separation membrane module in which a water separation membrane having at least one flow path extending in the up and down direction to cause a liquid 50 to pass through is provided with a liquid inlet at the bottom thereof and a liquid outlet at the top thereof; and a shell 11 defined by the outer surface of the water separation membrane module and the inner wall of the dehydrating apparatus body, wherein water in the liquid permeates the water separation membrane while the liquid rises in the water separation membrane, and moves in the shell, whereby the liquid is dehydrated; a pressure reducing device 13 for reducing the pressure of the shell 11; a pressure device for pressurizing the liquid before the liquid is fed to the water separation membrane module; and a heating device for heating the pressurized liquid.

10 Claims, 4 Drawing Sheets

(51) Int. Cl.
*B01D 61/10* (2006.01)
*B01D 61/36* (2006.01)
*B01D 63/06* (2006.01)
*C07C 29/76* (2006.01)

(52) U.S. Cl.
CPC ........ *B01D 2311/04* (2013.01); *B01D 2311/08* (2013.01); *B01D 2313/08* (2013.01); *B01D 2313/38* (2013.01); *B01D 2317/04* (2013.01); *B01D 2319/04* (2013.01)

(56) References Cited

U.S. PATENT DOCUMENTS

| | | | |
|---|---|---|---|
| 4,978,430 | A | 12/1990 | Nakagawa et al. |
| 4,997,462 | A | 3/1991 | Nakatani et al. |
| 5,105,029 | A | 4/1992 | Ninomiya et al. |
| 5,143,526 | A | 9/1992 | Lee et al. |
| 5,151,190 | A * | 9/1992 | Seiryo ............................ 210/640 |
| 5,294,345 | A | 3/1994 | Kaschemekat |
| 5,494,556 | A | 2/1996 | Mita et al. |
| 5,556,539 | A * | 9/1996 | Mita et al. ...................... 210/640 |
| 5,582,721 | A | 12/1996 | Mita et al. |
| 5,616,247 | A | 4/1997 | Mita et al. |
| 5,755,967 | A | 5/1998 | Meagher et al. |
| 5,868,906 | A | 2/1999 | Adams et al. |
| 6,210,464 | B1 | 4/2001 | Nakanishi et al. |
| 6,660,165 | B1 | 12/2003 | Hirabayashi et al. |
| 6,899,741 | B2 | 5/2005 | Nakamura et al. |
| 6,928,750 | B2 * | 8/2005 | Kashkoush et al. ............. 34/548 |
| 7,045,062 | B1 | 5/2006 | Aminabhavi et al. |
| 7,459,084 | B2 | 12/2008 | Baig et al. |
| 7,655,141 | B2 | 2/2010 | Bruschke et al. |
| 7,699,961 | B2 | 4/2010 | Ikeda et al. |
| 7,732,173 | B2 | 6/2010 | Mairal et al. |
| 7,732,967 | B2 | 6/2010 | Vollmer et al. |
| 7,871,520 | B2 | 1/2011 | Ma et al. |
| 7,892,321 | B2 | 2/2011 | Aagesen et al. |
| 8,002,874 | B2 | 8/2011 | Huang et al. |
| 8,128,787 | B2 | 3/2012 | Wynn et al. |
| 8,142,662 | B2 | 3/2012 | Osora et al. |
| 2003/0101866 | A1 | 6/2003 | Noack |
| 2004/0000521 | A1 | 1/2004 | Vane et al. |
| 2004/0211726 | A1 * | 10/2004 | Baig et al. ...................... 210/640 |
| 2004/0256212 | A1 | 12/2004 | Ikeda et al. |
| 2007/0112189 | A1 | 5/2007 | Ikeda et al. |
| 2007/0284307 | A1 * | 12/2007 | Lin ................................ 210/649 |
| 2008/0099400 | A1 | 5/2008 | Nemser et al. |
| 2014/0014583 | A1 | 1/2014 | Hanemaaijier |

FOREIGN PATENT DOCUMENTS

| | | |
|---|---|---|
| JP | 50-132896 U | 10/1975 |
| JP | 54-033279 | 3/1979 |
| JP | 58-011083 A | 1/1983 |
| JP | 58-021629 A | 2/1983 |
| JP | 60-202705 A | 10/1985 |
| JP | 62-011088 A | 1/1987 |
| JP | 62-237906 A | 10/1987 |
| JP | 63-278522 A | 11/1988 |
| JP | 01-236905 A | 9/1989 |
| JP | 2-71829 A | 3/1990 |
| JP | 02-229529 A | 9/1990 |
| JP | 2-273519 A | 11/1990 |
| JP | 2-059394 B2 | 12/1990 |
| JP | 04-281827 A | 10/1992 |
| JP | 4-313333 A | 11/1992 |
| JP | 05-103956 A | 4/1993 |
| JP | 06-254354 A | 9/1994 |
| JP | 06-277402 A | 10/1994 |
| JP | 06-287153 A | 10/1994 |
| JP | 06-304453 A | 11/1994 |
| JP | 07-124444 A | 5/1995 |
| JP | 9-220563 A | 8/1997 |
| JP | 10-180046 A | 7/1998 |
| JP | 11-156167 A | 6/1999 |
| JP | 2003-093828 A | 4/2003 |
| JP | 2003-530999 A | 10/2003 |
| JP | 2004-131024 A | 4/2004 |
| JP | 2004-255283 A | 9/2004 |
| JP | 2005-145773 A | 6/2005 |
| JP | 2007-045482 A | 2/2007 |
| JP | 2007-275690 A | 10/2007 |
| WO | 86/01425 A1 | 3/1986 |

OTHER PUBLICATIONS

Japanese Office Action dated Nov. 17, 2009 (mailing date), issued in corresponding Japanese Patent Application No. 2007-066287. X.
International Search Report of PCT/JP2008/054782, mailing Date of Apr. 22, 2008.
Japanese Office Action dated Jul. 28, 2009, issued in corresponding Japanese Patent Application No. 2007-305646.
International Search Report of PCT/JP2008/054791, mailing Date of Apr. 8, 2008.
Japanese Office Action, mailing date of Oct. 16, 2009, issued in corresponding Japanese Patent Application 2006-273918.
International Search Report of PCT/JP2008/054777, mailing date of Apr. 15, 2008.
International Search Report of PCT/JP2008/054790, Mailing Date of Apr. 22, 2008.
Japanese Office Action dated Jun. 24, 2011, issued in corresponding Japanese Patent Application No. 2007-066286.
Office Action dated Jul. 28, 2011 of U.S. Appl. No. 12/522,791.
European Search Report dated Dec. 5, 2011, issued in European Patent Application No. 08722178.4 (corresponding U.S. Appl. No. 12/522,791).
European Search Report dated Dec. 5, 2011, issued in European Patent Application No. 08722187.5 (corresponding U.S. Appl. No. 12/523,620).
European Search Report dated Dec. 5, 2011, issued in European Patent Application No. 08722186.7 (corresponding U.S. Appl. No. 12/522,831).
Extended European Search Report dated Aug. 14, 2012, issued in technically related European Patent Application No. 08722173.5 (6 pages), corresponding to U.S. Appl. No. 12/743,997.
U.S. Notice of Allowance dated Dec. 7, 2012, issued in U.S. Appl. No. 12/523,620.
U.S. Office Action dated Dec. 24, 2012, issued in U.S. Appl. No. 12/743,997.
U.S. Notice of Allowance dated May 12, 2014, issued in U.S. Appl. No. 14/053,161 (10 pages).
U.S. Non-Final Office Action dated Nov. 22, 2013, issued in U.S. Appl. No. 14/053,161 (22 pages).
US Office ACtion dated Jul. 23, 2013, issued in U.S. Appl. No. 12/522.791 (29 pages).
Canadian Notice of Allowance issued Jul. 9, 2013 in related Canadian application No. 2,706,047 (1 page).
European Notice of Allowance dated Jul. 23, 2013, issued in European Patent Application No. 08 722 173.5 (27 pages).
US Office Action dated Apr. 15, 2014, issued in U.S. Appl. No. 12/522,791 (18 pages).
U.S. Notice of Allowance dated Apr. 3, 2013, issued in U.S. Appl. No. 12/523,620.
US Office Action dated Apr. 2, 2013, issued in U.S. Appl. No. 12/743,997.
Canadian Notice of Allowance dated Mar. 8, 2013, issued in corresponding Canadian Patent Application No. 2,676,899 (1 page)(Corresponding to U.S. Appl. No. 12/523,620).
Partial European Search Report dated Sep. 28, 2012, issued in European Patent Application No. 12175826.2 (Corresponding to U.S. Appl. No. 12/522,791).

(56) References Cited

OTHER PUBLICATIONS

Canadian Office Action issued Jan. 4, 2013 in related Canadian application No. 2,706,047 (corresponding to U.S. Appl. No. 12/743,997).
Canadian Notice of Allowance issued Jan. 23, 2013 in related Canadian application No. 2,675,399 (corresponding to U.S. Appl. No. 12/522,831).
Extended European Search Report issued Feb. 11, 2013 in related European application No. 12175826.2 (Corresponding to U.S. Appl. No. 12/522,791).
Communication under Rule 71(3) EPC dated May 5, 2015, issued in European application No. 08 722 187.5 (corresponding to U.S. Patent No. 8,496,731) (48 pages).

* cited by examiner

DEHYDRATION SYSTEM AND DEHYDRATION METHOD

TECHNICAL FIELD

The present invention relates to a dehydration system and to a dehydration method. More particularly, the present invention relates to a dehydration system and to a dehydration method capable of efficiently dehydrating a mixture of water and ethanol or propanol which is in an azeotropic composition with water, a mixture of water and acid, and the like.

BACKGROUND ART

As a fuel source to replace fossil fuels, ethanol has attracted attention, and the market size thereof is predicted to be 55 million kiloliters in the year 2010. However, to use ethanol as a fuel, a crude product obtained from a biological raw material such as corn must be distilled and refined, and this must be dehydrated to at least 99.5 wt %.

Conventionally, in dehydrating, a dilute ethanol aqueous solution has been distilled in a distilling column so as to be concentrated to a point close to the azeotropic point of an aqueous ethanol, and then the solution has been dehydrated.

As a method for dehydrating an azeotrope, a method is available in which an entrainer is added to the azeotrope, and dehydration is accomplished by azeotropic distillation. However, the method requires a process in which a three-component azeotrope is distilled, and furthermore, the entrainer must be recovered. Therefore, the method has some drawbacks such as large amount of heat energy being required.

Another method is available in which plural molecular sieve tanks are arranged in parallel, and dehydration is accomplished while these tanks are switched over in a batch mode. This method also has a drawback in that the regeneration of the molecular sieve tank consumes substantial amounts of energy.

Furthermore, there has been known a method in which water is separated from a liquid mixture that is mutually completely soluble by a membrane separation process using the pervaporation method using a membrane separator (Patent Document 1: Japanese Unexamined Patent Application Publication No. 7-124444). The membrane separation process using the pervaporation method has advantages of high separation performance and energy saving in the separation of a liquid mixture that is mutually soluble.

Patent Document 1: Japanese Unexamined Patent Application Publication No. 7-124444

DISCLOSURE OF THE INVENTION

Problems to be Solved by the Invention

The membrane separation process using the pervaporation method is a promising method of refining ethanol fuel and the like, and the enhancement of performance thereof has been demanded for the purpose of practical use. In particular, it has been demanded to obtain a high-purity ethanol anhydride with higher efficiency.

It has been known that when a membrane separation process using the pervaporation method is accomplished by using a water separation membrane reactor, as the temperature of a liquid being treated increases, the permeation flux (unit: $kg/m^2h$) representing the membrane performance of a water separation membrane increases, and therefore the separation performance is improved. However, if a liquid mixture is heated to the gasification temperature for the purpose of improving the separation performance by raising the liquid temperature, there arises a problem in that the heating amount increases due to the heat of vaporization. Also, if the liquid mixture is heated to a temperature at which a mixed phase of gas and liquid is formed, the membrane is destroyed by cavitation.

Means for Solving the Problems

The present inventors discovered that by heating the liquid mixture to a high temperature while maintaining the liquid state, the permeation flux is increased, and as a result the membrane performance can be improved without the occurrence of the above problems, and they thereby completed the present invention.

The present invention may provide a dehydration system comprising a dehydrating apparatus comprising, in a dehydrating apparatus body, a water separation membrane module in which a water separation membrane having at least one flow path extending in the up and down direction to cause a liquid to pass through is provided with a liquid inlet at the bottom thereof and a liquid outlet at the top thereof; and a shell defined by the outer surface of the water separation membrane module and the inner wall of the dehydrating apparatus body, wherein water in a liquid permeates the water separation membrane to move to the shell while the liquid rises in the water separation membrane module, whereby the liquid is dehydrated; a pressure reducing device for reducing the pressure of the shell; a pressure device for pressurizing the liquid before the liquid is fed to the water separation membrane module; and a heating device for heating the pressurized liquid before the liquid is fed to the water separation membrane module.

In the dehydration system, the pressure device for pressurizing the liquid before the liquid is fed to the water separation membrane module may be provided upstream of the dehydrating apparatus, may be provided downstream thereof, or may be provided both upstream and downstream thereof. Like the pressure device provided upstream of the dehydrating apparatus, the pressure device provided downstream thereof can also feed the liquid to the dehydrating apparatus in a pressurized state.

In another modification, the dehydration system in accordance with the present invention may have a further feature that a liquid concentration measuring device is provided downstream of the dehydrating apparatus.

In still another modification, the dehydration system in accordance with the present invention may have a further feature that a liquid flow regulator, which is connected to the liquid concentration measuring device, is further provided upstream of the dehydrating apparatus.

In yet another modification, the dehydration system in accordance with the present invention may have a further feature that the dehydrating apparatus has at least two water separation membrane modules; at least two dehydrating apparatuses are connected in series; and a mixer for mixing the liquid recovered from the upstream dehydrating apparatus is further provided in a pipe for connecting the dehydrating apparatuses in series.

In another aspect, the present invention may provide a dehydration method in which a liquid is caused to flow from a bottom inlet of a water separation membrane, which has at least one flow path extending in the up and down direction, toward an top outlet; and the pressure of the outside of the water separation membrane is reduced to cause water in the liquid to permeate to the outside of the water separation membrane, wherein that the liquid is fed to the water separation membrane in a state of being heated under pressurization.

In another modification, the dehydration method in accordance with the present invention may further comprise the steps of measuring the concentration of anhydride or water in the dehydrated liquid, and regulating the quantity of liquid fed to the water separation membrane in response to the concentration.

In still another mode, the dehydration method in accordance with the present invention may further comprise the steps of dehydrating the liquid by using at least two water separation membranes arranged in parallel; mixing the liquid recovered from the water separation membrane; and dehydrating the mixed liquid by a further water separation membrane.

Advantages of the Invention

According to the present invention, there are provided a dehydration system and a dehydration method in which by feeding a liquid to the water separation membrane module at a high temperature under pressurization, the membrane separation performance is enhanced without the occurrence of problems which may be caused by the gasification of liquid, whereby high dehydration performance is realized.

DESCRIPTION OF SYMBOLS

Figure 1:
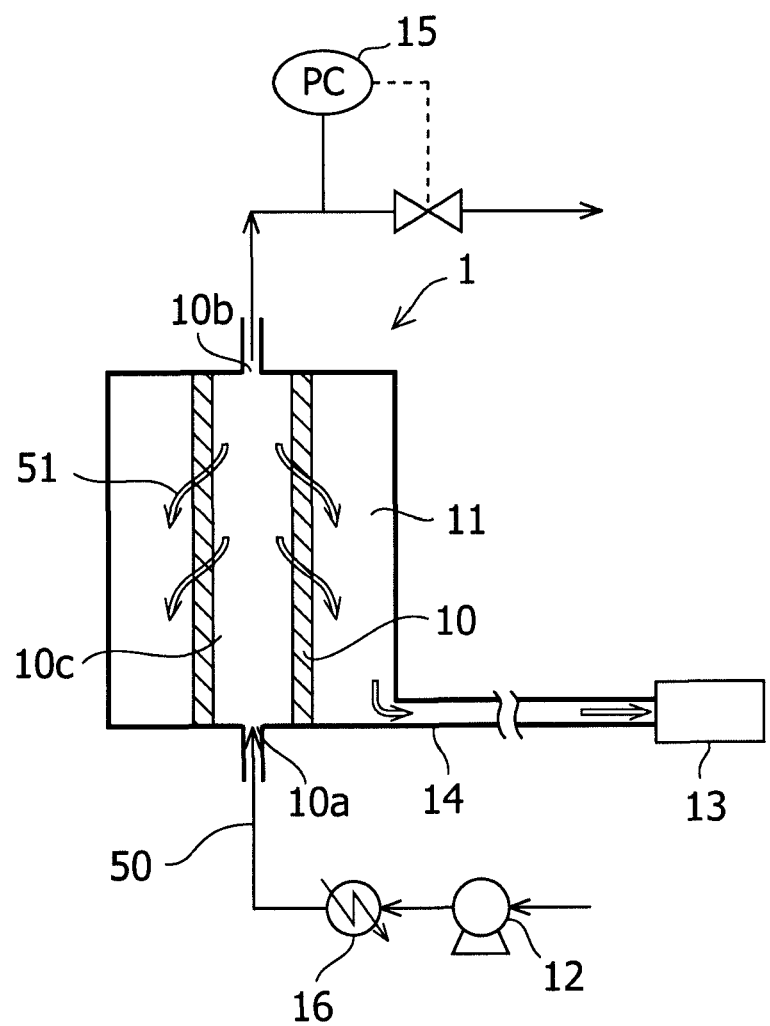
FIG. 1 is a schematic view for explaining one embodiment of a dehydration system in accordance with the present invention.

1 . . . dehydrating apparatus
2 . . . liquid concentration measuring device
3 . . . flow regulator
4 . . . valve
5 . . . mixer
10, 110, 210 . . . water separation membrane module
10a, 110a, 210a . . . liquid inlet
10b, 110b, 210b . . . liquid outlet
10c, 110c, 210c . . . flow path
10d, 110d, 210d . . . water separation membrane
11 . . . shell
12 . . . pressure rising pump
13 . . . pressure reducing device
14 . . . duct
15 . . . pressure regulator
16 . . . heat exchanger
50 . . . liquid
51 . . . water vapor

BEST MODE FOR CARRYING OUT THE INVENTION

A dehydrating apparatus, a dehydration system, and a dehydration method in accordance with the present invention will now be described in more detail with reference to embodiments thereof.

FIG. 1 shows one embodiment of the dehydration system in accordance with the present invention.

The dehydration system shown in FIG. 1 includes, as major components, a dehydration apparatus 1 provided with a water separation membrane module 10, a shell 11, and a vacuum duct 14 in a dehydrating apparatus body; a pressure reducing device 13, a pressure rising pump 12, a heat exchanger 16, and a pressure regulator 15.

The water separation membrane module 10 of the dehydration apparatus 1, which is provided in the dehydrating apparatus body, consists of a water separation membrane 10d, and is provided with a liquid inlet 10a on the lower side in the vertical direction and a liquid outlet 10b on the upper side therein. In the water separation membrane module 10, one or more flow paths 10c for a liquid, which are hollow portions extending in the up and down direction to allow the liquid to pass through, are formed. The shell 11 is located around the side surface of the water separation membrane module 10. In the shell 11, the vacuum duct 14 is provided. The vacuum duct 14 is connected to the pressure reducing device 13.

The water separation membrane module 10 separates the liquid 50, which is a mixture of anhydride and water, into anhydride and water. As such a water separation membrane module, various types have been known and are commercially available. As the water separation membrane module 10 of the present embodiment, a monolith-type or tubular-type water separation membrane module can be used as one example.

Figure 2A:
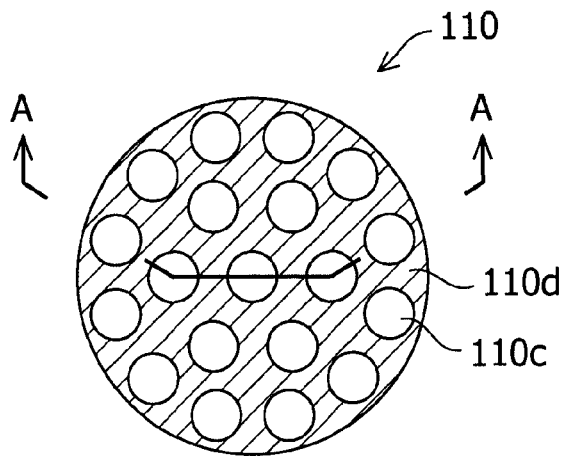
FIGS. 2A and 2B are a schematic views for explaining one embodiment of a water separation membrane module in accordance with the present invention.
Figure 2B:
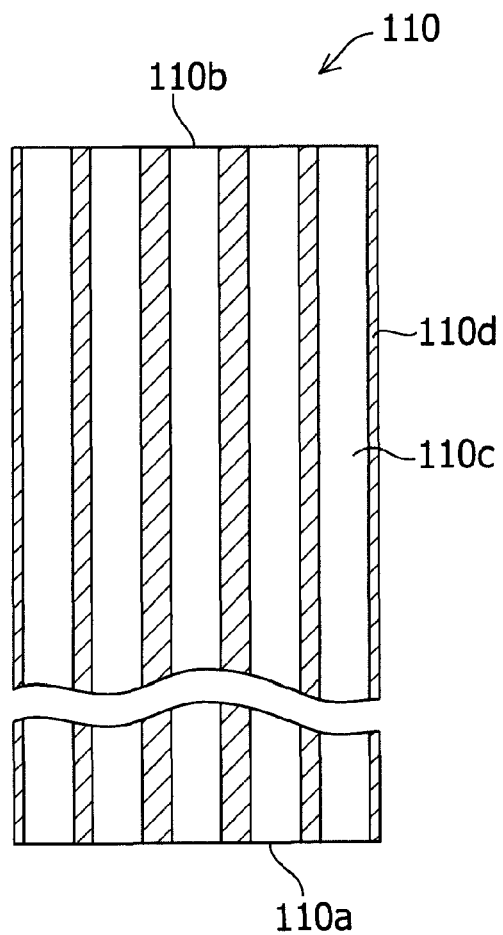

A monolith-type water separation membrane module 110 shown FIGS. 2A and 2B is explained as one example. FIG. 2B is a sectional view taken along the line A-A of FIG. 2A. In the monolith-type water separation membrane module 110, a plurality of liquid flow paths 110c, which are one or more hollow portions extending in the up and down direction to allow the liquid to pass through, are provided in a columnar water separation membrane 110d. In the water separation membrane of this type, the liquid flow path 110c in the water separation membrane is called a primary side or a feed side of the membrane, and the outside of the water separation membrane 110d is called a secondary side or a permeate side of the membrane.

In membrane separation process using the pervaporation method using such a water separation membrane module, the water separation membrane module 110 is preferably placed so that the direction of the flow path is parallel with the vertical direction. The liquid 50 is fed from a liquid inlet 110a on the lower side in the vertical direction while the pressure on the permeate side of the water separation membrane module 110 is reduced, being caused to flow in the direction reverse to the gravity, and is recovered from a liquid outlet 110b on the upper side in the vertical direction. By this procedure, water in the liquid 50 is converted into water vapor 51, and the water vapor 51 is drawn out to the permeate side from the side surface of the water separation membrane 110d. As a result, the liquid 50 recovered from the liquid outlet 110b of the water separation membrane module is dehydrated.

The figures of the monolith-type water separation membrane module 110 shown in FIGS. 2A and 2B are schematic views. As one example, a water separation membrane module provided with thirty holes, each having a diameter of 3 mm in a columnar water separation membrane having a diameter of 30 mm, can be used. As another example, a water separation membrane module provided with two hundred holes, each having a diameter of 2 mm in a columnar water separation membrane having a diameter of 150 to 200 mm, can be used. The length of the water separation membrane module can be determined appropriately by one skilled in the art according to the desired membrane performance. As one example, a water separation membrane module having a length ranging from 150 mm to 1 m can be used.

Figure 3A:
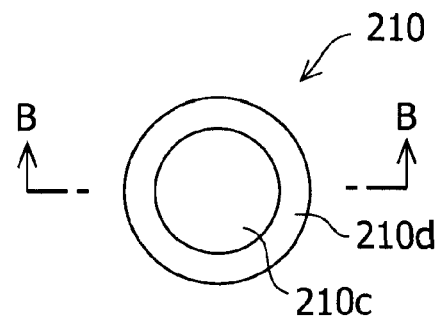
FIGS. 3A and 3B are schematic views for explaining another embodiment of a water separation membrane module in accordance with the present invention.
Figure 3B:
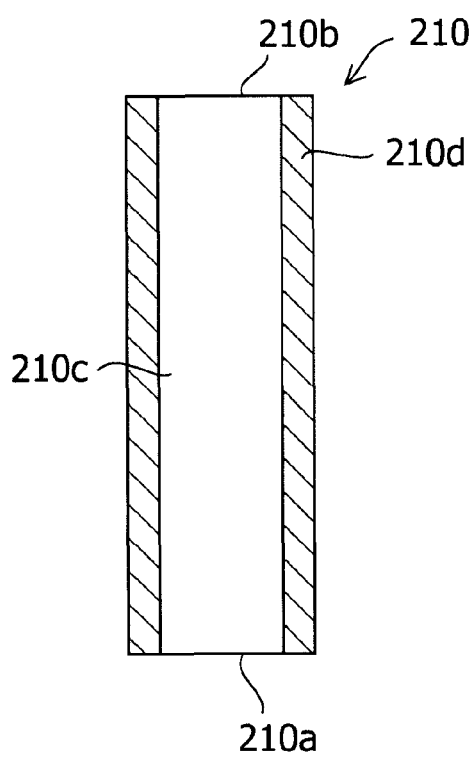

As another example, a tubular-type water separation membrane module 210 shown in FIGS. 3A and 3B is explained. FIG. 3B is a sectional view taken along the line B-B of FIG. 3A. The tubular-type water separation membrane module 210 is a tubular water separation membrane 210d provided with only one liquid flow path 210c therein. The tubular-type water separation membrane module 210 has the same installation mode and operational advantage as those of the monolith-type water separation membrane module. As one example, a tubular-type water separation membrane module having an outer diameter of 10 mm and an inner diameter of 7 mm can be used. As another example, a tubular-type water separation membrane module having an outer diameter of 30 mm and an inner diameter of 22 mm can be used. Regarding the length, as one example, a tubular-type water separation membrane module having a length ranging from 150 mm to 1 m can be used.

As the water separation membrane constituting the water separation membrane module, an inorganic porous membrane in which a nano-order or smaller pore diameter is controlled precisely can be used. The porous membrane having fine pores achieves a molecule sieving effect of allowing small-molecule gases to pass through and excluding large-molecule gases, and exhibits a behavior of activation diffusion in which the permeation factor thereof increases with an increase in temperature. An example of a porous membrane having fine pores may include a carbon membrane, silica membrane, and zeolite membrane. In the present embodiment, as the water separation membrane, a silica- or zeolite-based inorganic water separation membrane having 10-angstrom or smaller fine pores may be suitable.

The inorganic water separation membrane described in Japanese Patent No. 2808479 can also be applied to the present embodiment. The inorganic water separation membrane described in Japanese Patent No. 2808479 is an acid-resistant composite separating membrane obtained by carrying silica gel, which is obtained by hydrolysis of alkoxysilane having an ethoxy group or methoxy group, in the fine pores of an inorganic porous body.

The shape, size, and material of the water separation membrane module can be selected appropriately by one skilled in the art according to the purpose of use. In the present embodiment, the water separation membrane module is preferably formed of a water separation membrane material having a high physical strength. This is because the water separation membrane module is used in the state in which a pressurized liquid is fed into the flow path therein.

The shell 11 in the dehydrating apparatus body is located on the permeate side of the water separation membrane at the periphery of the water separation membrane module. The shell 11 serves as a flow path for the water vapor 51 released from the side surface of the water separation membrane module 10. In the present embodiment, the shell 11 is a space defined by the side surface of the water separation membrane module 10 and the inner wall of the dehydrating apparatus body. The shell 11 is configured so that the liquid, before being fed to the water separation membrane module 10, or the liquid 50 recovered from the water separation membrane module 10, does not flow into the shell 11.

The shell 11 is provided with the vacuum duct 14. The vacuum duct 14 serves as a connection port for connection with the pressure reducing device 13. The vacuum duct 14 recovers the water vapor 51 released into the shell 11. The vacuum duct 14 may be provided horizontally, or it may be provided downward in the vertical direction. The direction of the vacuum duct 14 is not subject to any restriction. The installation position and the number thereof are not subject to any restriction.

The pressure reducing device 13 is a means for reducing the pressure of the shell 11 to aspirate the water vapor 51 released from the water separation membrane module 10. The pressure reducing device 13 may be any pressure reducing devices capable of reducing the pressure to about 10 to 100 torr (1333.22 to 13332.2 Pa). As the pressure reducing device 13, an ordinary pressure-reducing pump or the like can be used.

The pressure rising pump 12 is a pressure device provided upstream of the dehydrating apparatus 1 and the heat exchanger 16. The pressure rising pump 12 is used to pressurize the liquid 50 to be dehydrated to a predetermined pressure. As the pressure device, an ordinary pressure rising pump or the like can be used. The pressure rising pump 12 may be a pump capable of pressurizing the liquid 50 preferably to a pressure ranging from 2 to 10 atm.

The heat exchanger 16 is a heating device provided upstream of the dehydrating apparatus 1 and downstream of the pressure rising pump 12. The heat exchanger 16 heats the liquid 50, which has been pressurized to the predetermined pressure by the pressure rising pump 12 located upstream thereof, preferably to a temperature that is close to the azeotropic point and lower than the azeotropic point under such a pressure. As the heating device, an ordinary heat pump or heater or the like can be used.

The pressure regulator 15 is a pressure device provided downstream of the dehydrating apparatus 1. The pressure regulator 15 measures the pressure of the liquid 50 recovered from the dehydrating apparatus 1. The pressure regulator 15 opens or closes a valve downstream thereof as necessary to regulate the pressure to a predetermined value.

One embodiment of a method for dehydrating a liquid by using the dehydration system of the present embodiment is explained. The liquid 50 to be dehydrated by the dehydration system of the present embodiment is generally a mixture of water and a liquid miscible with the water. Specifically, the liquid 50 to be dehydrated includes a mixture of ethanol and water, a mixture of propanol and water, and a mixture of an acid such as acetic acid and water. The liquid may contain alcohol or acid with a concentration of 80 to 95 wt %. Such concentrations are attained by treating a mixture used as a raw material by using a distilling column or an alcohol selective transmission membrane. The dehydration method is explained by taking a mixture of ethanol useful as a fuel and water as one example of the liquid to be dehydrated. The concentration of ethanol in the liquid fed to the dehydrating apparatus of the present embodiment is preferably 95 wt %.

As shown in FIG. 1, the liquid 50, which is a mixture of 95 wt % ethanol and 5 wt % water, is pressurized by the pressure rising pump 12. The liquid 50 is preferably pressurized so that the pressure thereof is higher than the atmospheric pressure. Specifically, the liquid 50 is pressurized preferably to 1.5 to 10 atm, more preferably to 2 to 3 atm. However, the degree of pressurization can be determined appropriately by one skilled in the art depending on the physical strength of the water separation membrane used.

The pressurized liquid 50 is preferably heated by a heat exchanger or the like. The temperature of the liquid may be determined depending on the pressure thereof. The pressurized liquid 50 is preferably heated to a temperature that is close to the azeotropic point and lower than the azeotropic point under the predetermined pressure. For example, the liquid 50 is preferably heated to a temperature range of a temperature 10 to 30° C. lower than the azeotropic point to a temperature lower than the azeotropic point. The temperature to which the liquid 50 is heated must be lower than the decomposition temperature of an anhydride contained in the liquid 50. As one example, for the mixture of ethanol and water, which is a favorable liquid to be dehydrated, the temperature thereof at the supply time may be 90 to 150° C. Since the decomposition temperature of ethanol is 200° C., the temperature of the liquid 50 containing ethanol at the supply time is lower than 200° C.

The liquid 50 having been heated is fed from the liquid inlet 10*a* of the water separation membrane module 10. The flow rate of the liquid 50 is preferably 0.5 to 1 msec. However, the flow rate can be determined appropriately by one skilled in the art depending on the permeation flux.

The liquid 50 is fed to the water separation membrane module 10, while reducing the pressure of the shell 11. The pressure of the shell 11 is preferably reduced to about 10 to 100 torr (1333.22 to 13332.2 Pa). This is because the permeation is accelerated by a differential pressure between the feed side and the permeate side of water separation membrane. In the present embodiment, since the liquid on the feed side is pressurized, the differential pressure between the feed side and the permeate side is large, especially compared with the case in which the liquid 50 is fed under atmospheric pressure, so that the permeation of the water vapor 51 from the water separation membrane module 10 is accelerated more.

The liquid 50 passes through the flow path 10*c* upward from the bottom to the top of the water separation membrane module 10. During this time, water contained in the liquid 50 flowing in the flow path 10*c* is taken out to the shell 11 as the water vapor 51 via the water separation membrane 10*d*. For the liquid 50 recovered from the liquid outlet 10*b*, the concentration of contained water decreases. The pressure of the liquid 50 is monitored by the pressure regulator 15 provided downstream of the dehydrating apparatus 1, and is regulated to the optimal value as necessary. The water vapor 51 released into the shell 11 is recovered from the vacuum duct 14. The recovered water vapor 51 is condensed by a cooler downstream.

In the present embodiment, the dehydrating apparatus 1 provided with only one water separation membrane module 10 is shown for ease of explanation. However, the dehydrating apparatus 1 can be provided with plural water separation membrane modules 10, which are connected in parallel, in the dehydrating apparatus body. In such a configuration as well, the shell 11 provides one continuous space defined by the inner wall of the dehydrating apparatus body and the outer surfaces of the water separation membrane modules 10, and the water vapor can be moved therein. By providing the plural water separation membrane modules, which are connected in parallel, in the dehydrating apparatus body, the quantity of liquid treated at a time by one dehydrating apparatus can be increased.

Furthermore, in the present embodiment, a modification in which the pressure rising pump is provided upstream of the dehydrating apparatus, and the pressure regulator is provided downstream of the dehydrating apparatus, that is, a modification in which two pressure devices are provided both upstream and downstream of the dehydrating apparatus has been shown. However, for example, in the case in which the original pressure of the raw material is high, the system may be such that the pressure rising pump upstream of the dehydrating apparatus is not provided, and the pressure is regulated by the downstream pressure regulator only. Alternatively, the system may also be such that the downstream pressure regulator is not provided, and the pressure is regulated by the upstream pressure rising pump only. In either case, the pressure device can make the liquid fed to the dehydrating apparatus be in a pressurized state.

As a further modification of the present embodiment, a supply port and a discharge port for an inert gas can be provided in the shell in place of the pressure reducing device connected to the shell 11 via the duct. In such a modification, by causing the inert gas to flow in the shell, the same operation and effects as those of the embodiment shown in FIG. 1 can be performed. As the inert gas, nitrogen or argon can be used, as an example. The flow rate of the supplied inert gas is preferably, for example, a flow rate faster than 5 to 15 msec.

Furthermore, as another modification of the present embodiment, the dehydration system may be such that a heating device is provided in the upper portion of the shell 11 near the liquid outlet 10*b* of the water separation membrane module 10, and a duct connected with the pressure reducing device is provided in the lower portion of the shell 11 near the liquid inlet 10*a* of the water separation membrane module 10. The dehydration system may be such that a device for supplying a heated inert gas is further provided in the upper portion of the shell 11 near the liquid outlet 10*b* of the water separation membrane module 10. In the modification, heat convection directed from the upper portion to the lower portion is formed in the shell 11. By the heat convection, the liquid 10 flowing in a portion near the liquid outlet 10*b* of the water separation membrane module 10 is heated from the shell 11 via the water separation membrane, so that the permeation flux near the liquid outlet 10*b* of the water separation membrane module 10 can be increased.

In the water separation membrane module extending in the up and down direction of the present embodiment, there is seen a phenomenon in which, as the liquid approaches the outlet, the liquid temperature is decreased by the heat of vaporization of water. Consequently, the permeation flux decreases. By heating the water separation membrane module 10 by the heating device provided in the shell 11, the temperature of the liquid to be dehydrated is prevented from decreasing, and therefore the permeation flux can be maintained at a high level.

According to the method of the present embodiment shown in FIG. 1, the liquid 50 is fed to the water separation membrane module 10 after being pressurized, by which the membrane performance can be enhanced.

Figure 4:
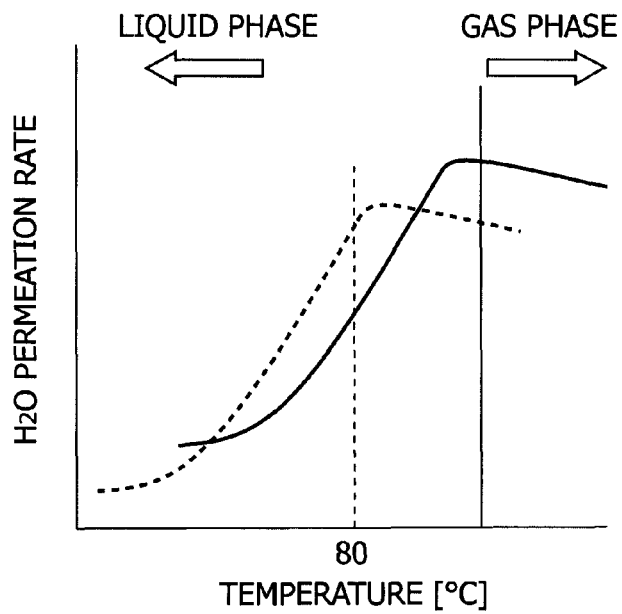
FIG. 4 is a graph showing the relationship between the temperature and pressure of a liquid and the permeation flux thereof.

It has been known that the membrane performance can be evaluated by the permeation flux, and the permeation flux is proportional to the temperature. FIG. 4 is a graph schematically showing the relationship between temperature and permeation flux at different pressures. The broken line indicates the relationship between temperature and permeation flux of a liquid mixture at the atmospheric pressure. The azeotropic point of the liquid mixture at the atmospheric pressure is about 80° C. At a temperature higher than the azeotropic point, a state of containing gas is formed. Therefore, if the liquid having a temperature not lower than 80° C. at the atmospheric pressure is fed to the membrane reacting module 10, although a high permeation flux can be provided, there occurs disadvantageously problems of cavitation and increased heating amount. The solid line indicates the relationship between temperature and permeation flux of the liquid at a pressure of 2 atm. The azeotropic point of the liquid mixture at 2 atm is about 100° C., and if the liquid mixture is heated to about 100° C., the mixture of ethanol and water remains in a liquid state. The permeation flux at about 100° C. is about 20% higher than the permeation flux at about 80° C., so that the water separation performance can be enhanced. Since a differential pressure between the feed side and the permeate side increases as compared with the case at the atmospheric pressure, the permeability advantageously increases by about 20%.

Thus, by heating the liquid 50 fed to the water separation membrane module 10 to a temperature that is close to the azeotropic point and lower than the azeotropic point under pressurization, in the water separation membrane module 10, a high permeation flux can be obtained, and therefore the membrane performance can be enhanced without the occurrence of problems caused by the vaporization of the liquid 50. Therefore, dehydration can be performed until the concentration of ethanol in the liquid 50 becomes not lower than 99.7 wt %, that is, a concentration suitable for a fuel.

Figure 5:
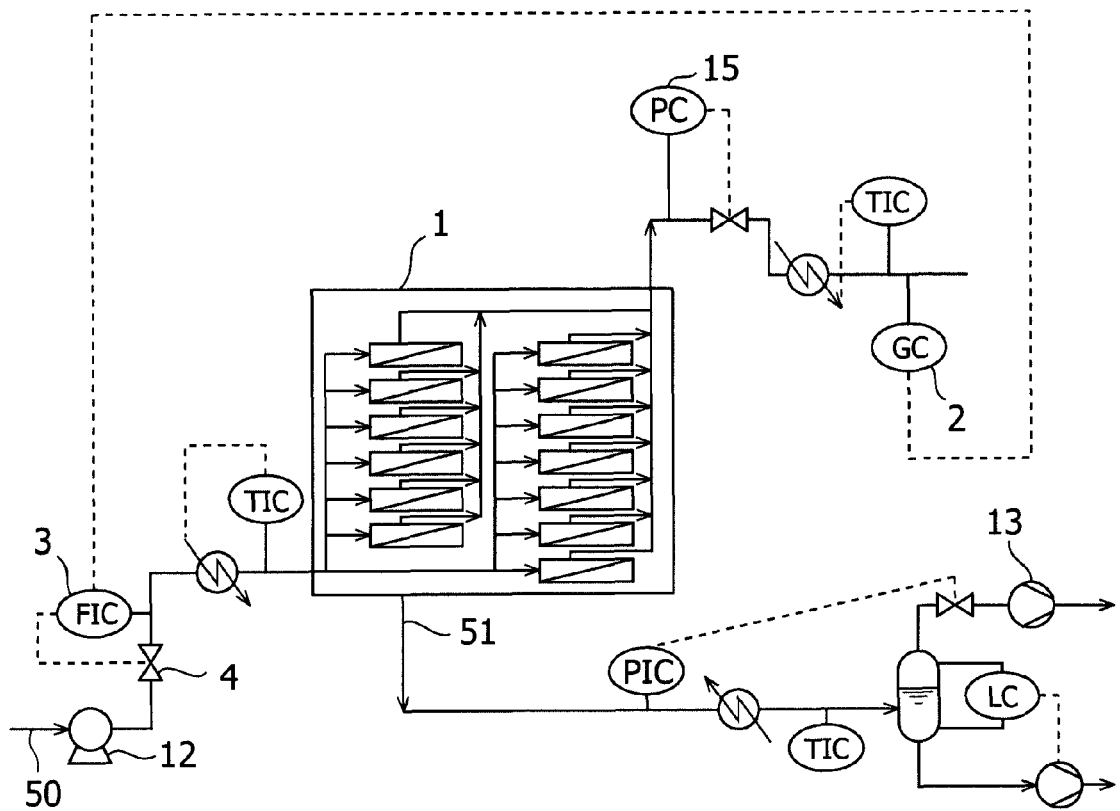
FIG. 5 is a schematic view for explaining another embodiment of a dehydration system in accordance with the present invention.

FIG. 5 shows another embodiment of the dehydration system in accordance with the present invention.

The dehydration system shown in FIG. 5 includes the dehydrating apparatus 1, a liquid concentration measuring device 2, a flow regulator 3, the pressure reducing device 13, and the pressure rising pump 12 as major components. The pressure reducing device 13 is connected to the shell 11 of the dehydrating apparatus 1. The liquid concentration measuring device 2 is provided downstream of the dehydrating apparatus 1. The pressure rising pump 12 and the flow regulator 3 are provided upstream of the dehydrating apparatus 1. The liquid concentration measuring device 2 and the flow regulator 3 are connected to each other.

The dehydrating apparatus 1 may be a dehydrating apparatus of the embodiment shown in FIG. 1 or the modification thereof, and may have the same configuration and operation. The figure of the dehydrating apparatus 1 shown in FIG. 5 is a schematic view, in which the orientation of liquid flow, the installation directions of the water separation membrane modules, and the positions of the liquid inlet and liquid outlet are not shown exactly.

The liquid concentration measuring device 2 measures the concentration of anhydride or water contained in the liquid recovered from the dehydrating apparatus 1. Specifically, a gas chromatograph, a densitometer, or the like can be used. A measuring device capable of making online measurements is preferably used.

The flow regulator 3 regulates the quantity of the liquid 50 fed to the dehydrating apparatus 1. As the flow regulator 3, a flow regulator that is capable of controlling a valve 4 so as to increase or decrease the quantity of the liquid 50 fed to the dehydrating apparatus 1 in response to the concentration information sent from the concentration measuring device 2 can be used.

One modification of a method for dehydrating the liquid 50, which is a mixture of ethanol and water, by using the dehydration system of the above-described embodiment is explained.

As shown in FIG. 5, the liquid 50 having an ethanol concentration of 95 wt % is pressurized by the pressure rising pump 12, and is fed to the dehydrating apparatus 1 through the heat exchanger 16. In the dehydrating apparatus 1, water is separated from the liquid 50 as the water vapor 51, and the liquid 50 having increased ethanol concentration is recovered. The gas chromatograph 2, which is the liquid concentration measuring device provided downstream of the dehydrating apparatus 1, measures the concentration of ethanol or water contained in the recovered liquid 50. The measurement of ethanol or water concentration may be made online at all times. The gas chromatograph 2 sends the measurement result to the flow regulator 3 connected to the gas chromatograph 2. The flow regulator 3 regulates the quantity of the liquid 50 fed to the dehydrating apparatus 1 in response to the measurement result of ethanol concentration. Specifically, when the ethanol concentration is low, the quantity of the liquid 50 fed to the dehydrating apparatus 1 is decreased by the operation of the valve 4. By this procedure, the ethanol concentration at the outlet of the dehydrating apparatus 1 is monitored, and this is fed back to the flow regulator 3, by which a system capable of obtaining ethanol of stable quality can be achieved.

As a further modification of the embodiment shown in FIG. 5, a dehydration system that includes the liquid concentration measuring device only and does not include a flow regulator can also be used. In such a modification, the liquid concentration measuring device, such as a gas chromatograph, can merely monitor the concentration of the recovered ethanol, and in some cases, can act as a barometer of the replacement time of the water separation membrane, for example.

According to the embodiment shown in FIG. 5 and the modification thereof, by providing the liquid concentration measuring device 2, the concentration of anhydride, such as ethanol, or water at the outlet of the dehydrating apparatus 1 can be detected, so that anhydride of stable quality can be obtained.

Figure 6:
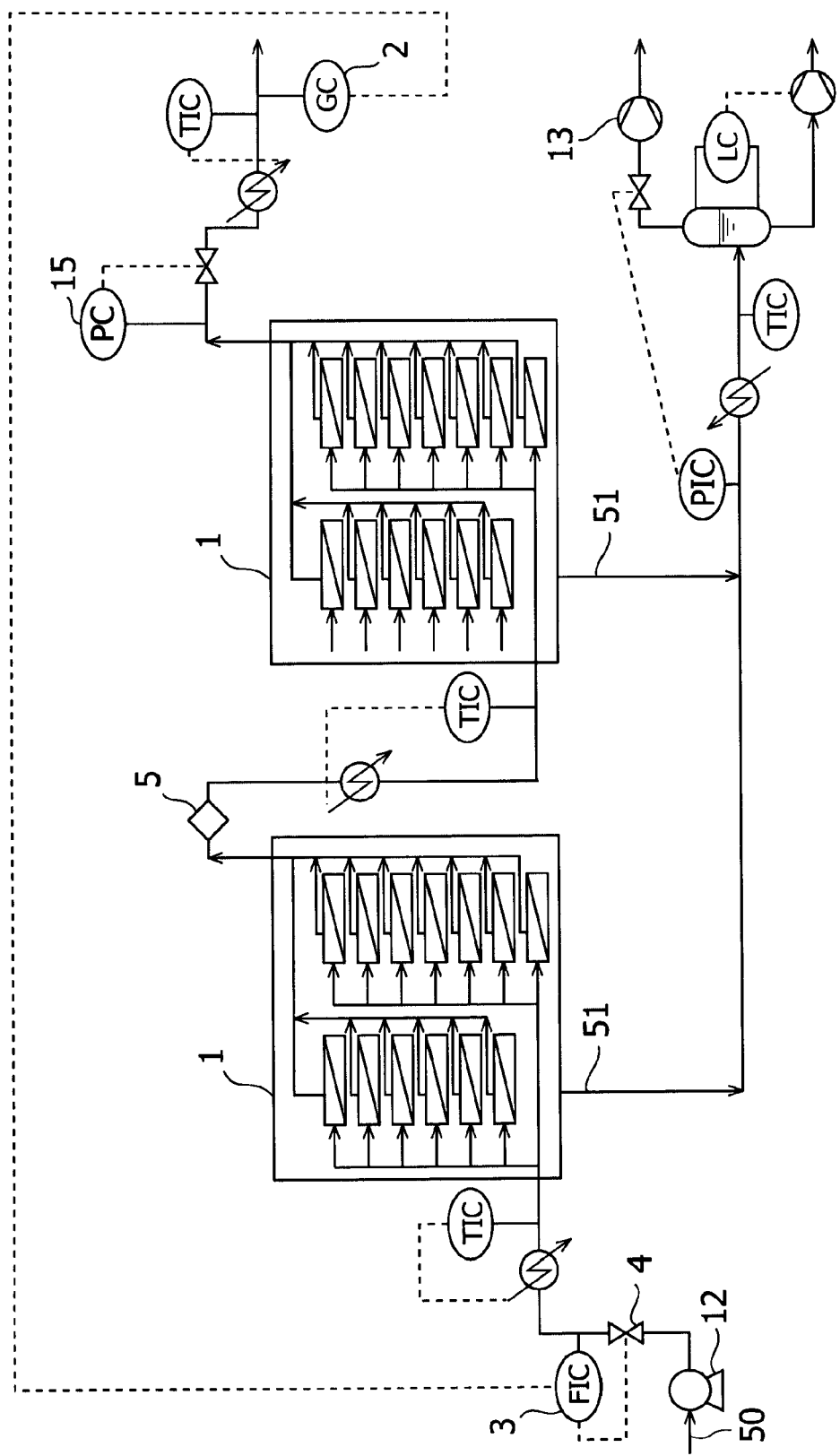
FIG. 6 is a schematic view for explaining still another embodiment of a dehydration system in accordance with the present invention.

FIG. 6 shows another embodiment of the dehydration system in accordance with the present invention.

The dehydration system shown in FIG. 6 includes a first dehydrating apparatus 1, a second dehydrating apparatus 1, a mixer 5, the liquid concentration measuring device 2, the flow regulator 3, the pressure reducing device 13, and the pressure rising pump 12 as major components. The two dehydrating apparatuses 1 are connected in series by a pipe. The mixer 5 is provided downstream of the first dehydrating apparatus and upstream of the second dehydrating apparatus.

The dehydrating apparatus 1 may be a dehydrating apparatus of the embodiment shown in FIG. 1 and modifications thereof, and may have the same configuration and operation. In particular, in the dehydration system shown in FIG. 6, the first dehydrating apparatus 1 is of a parallel treatment type such that plural water separation membrane modules 10 are connected in parallel in the apparatus body.

The mixer 5 is used to mix the dehydrated liquid that is recovered from the first dehydrating apparatus 1. As the mixer 5, for example, a blade-type device provided in the pipe can be used.

One modification of a method for dehydrating a mixture of ethanol and water by using the dehydration system of the above-described embodiment is explained.

As shown in FIG. 6, the liquid 50 containing 95 wt % ethanol is pressurized by the pressure rising pump 12, preferably being heated by the heat exchanger 16, and is sent into the first dehydrating apparatus 1. In the first dehydrating apparatus 1, water is separated from the liquid 50 as the water vapor 51 by the water separation membrane modules, and the liquid 50 having increased ethanol concentration is recovered. In some cases, the liquid 50 may have a different ethanol concentration depending on the individual differences between the water separation membrane modules. Then, the liquid 50 from each module is collected at one pipe and is supplied to the mixer 5. In the mixer 5, the liquid 50 is mixed sufficiently so that the concentration becomes uniform, and this is fed to the second dehydrating apparatus 1. In the second dehydrating apparatus 1, water is further separated from the liquid 50 as the water vapor 51, and the dehydrated ethanol with a higher purity is recovered.

As a modification of the above-described embodiment, a dehydration system in which three or more dehydrating apparatuses 1 are connected in series may also be used. In this case as well, likewise, the mixers are provided upstream of the second and subsequent dehydrating apparatuses. That is to say, the mixer is provided between the adjacent two dehydrating apparatuses in series. The dehydration system of the present embodiment may be a system that does not include the liquid concentration measuring device 2 and the flow regulator 3.

Furthermore, in the embodiment shown in FIG. 6, the pressure rising pump is provided upstream of the first dehydrating apparatus only, and the pressure regulator is provided downstream of the second dehydrating apparatus only. However, for each of the dehydrating apparatuses, the pressure rising pump can be provided upstream, and the pressure regulator can be provided downstream.

According to the embodiment shown in FIG. 6 and the modification thereof, by providing the mixer 5, the liquid 50 can be fed to the downstream dehydrating apparatus 1 after the variations in concentration of anhydride in the liquid 50 recovered from the water separation membrane module, which may be generated in the dehydrating apparatus 1 provided with the plurality of water separation membrane modules, are eliminated, and the recovered liquid 50 is made uniform. Without the mixing by the mixer 5, the dehydration in the first dehydrating apparatus 1 may become useless. For example, in the case in which the recovered liquid from some water separation membrane modules achieve an anhydride concentration of 99.9% which is over the target concentration, and the recovered liquid from other water separation membrane modules achieve an anhydride concentration of 97.0% which is below the target concentration, if the mixer 5 is absent, the liquid 50 having different concentrations is fed to the second dehydrating apparatus as they are. At this time, even if the liquid having an anhydride concentration of 99.9% were fed to the water separation membrane modules of the second dehydrating apparatus and the dehydration procedure were further conducted, further dehydration effect may not be achieved, and the procedure would be useless. On the other hand, even if the liquid having an anhydride concentration of 97.0% were fed to the water separation membrane modules of the second dehydrating apparatus and the dehydration procedure were further conducted, the target concentration cannot be reached, and in some cases, the finally obtained anhydride concentration does not reach the target concentration. In contrast, in the case in which the anhydride concentration in the liquid 50 from each of the water separation membrane module made uniform by the mixer 5, and this liquid 50 is fed to the second dehydrating apparatus 1, at least a useless procedure is not performed, and the dehydration effect in the first dehydrating apparatus 1 is put to good use in the next dehydrating apparatus 1. Thus, by providing the mixer 5, the dehydration effect in the first dehydrating apparatus 1 can be reliably reflected in the subsequent dehydrating apparatus, and the dehydration system can be stabilized overall.

The invention claimed is:

1. A dehydration system comprising:
a dehydrating apparatus comprising, in a dehydrating apparatus body,
a water separation membrane module in which a monolith-type or tubular-type water separation membrane having at least one flow path extending parallel to the up and down direction to cause a liquid to pass through the water separation membrane in a direction reverse to gravity is provided with a liquid inlet at the bottom thereof and a liquid outlet at the top thereof; and
a shell defined by the outer surface of the water separation membrane module and the inner wall of the dehydrating apparatus body, wherein
water in the liquid permeates the water separation membrane to move to the shell while the liquid rises in the water separation membrane, whereby the liquid is dehydrated, the shell being configured so that the liquid, before being fed to the water separation membrane module, or the liquid recovered from the water separation membrane module, does not flow into the shell, so that heat convection directed from the upper portion to the lower portion is formed in the shell;
a pressure reducing device for reducing the pressure of the shell;
a pressure device for pressurizing the liquid before the liquid is fed to the water separation membrane module; and
a heating device for heating the pressurized liquid before the liquid is fed to the water separation membrane module,
wherein the water separation membrane is a silica- or zeolite-based inorganic water separation membrane, and
wherein the dehydrating apparatus further comprises:
a) a heating device provided in the upper portion of the shell near the liquid outlet of the water separation membrane, or a device for supplying a heated inert gas into the shell provided in the upper portion of the shell near the liquid outlet of the water separation membrane; and
b) a duct connected with the pressure reducing device, which duct is provided in the lower portion of the shell near the liquid inlet of the water separation membrane.

2. The dehydration system according to claim 1, further comprising a liquid concentration measuring device downstream of the dehydrating apparatus.

3. The dehydration system according to claim 2, further comprising a liquid flow regulator, which is connected to the liquid concentration measuring device, upstream of the dehydrating apparatus.

4. The dehydration system according to claim 1, wherein
the dehydrating apparatus has at least two water separation membrane modules;
at least two dehydrating apparatuses are connected in series; and
a mixer for mixing the liquid recovered from the upstream dehydrating apparatus is further provided in a pipe for connecting the two dehydrating apparatuses.

5. A dehydration method comprising:
Passing a liquid through the dehydration system as recited in claim 1; and
Reducing the pressure of the outside of the water separation membrane so that water in the liquid permeates the water separation membrane to the outside, wherein the liquid is fed to the water separation membrane in a state of being heated under pressurization.

6. The dehydration method according to claim 5, further comprising the steps of:
measuring the concentration of anhydride or water in the dehydrated liquid; and
regulating the quantity of the liquid fed to the water separation membrane in response to the concentration.

7. The dehydration method according to claim 5 or 6, further comprising the steps of:
accomplishing dehydration by using at least two water separation membranes arranged in parallel;
mixing the liquid recovered from the water separation membrane; and
hydrating the mixed liquid further by using the water separation membrane.

8. The dehydration system according to claim 1, wherein the pressure device pressurizes the liquid to a pressure ranging from 2 to 10 atm.

9. The dehydration system according to claim 1, wherein the pressure reducing devices reduces the pressure of the shell to about 10 to 100 Torr.

10. The dehydration system according to claim 1, wherein the silica- or zeolite-based inorganic water separation membrane has 10 angstrom or smaller fine pores.

* * * * *